United States Patent [19]

Borris et al.

[11] Patent Number: 5,233,050

[45] Date of Patent: Aug. 3, 1993

[54] ANTIMIGRAINE ALKYL INDOLE

[75] Inventors: Robert P. Borris, Glen Gardner; Yiu-Kuen T. Lam, Plainsboro; Lawrence Koupal, Colonia, all of N.J.

[73] Assignee: Merck & Co., Inc., Rahway, N.J.

[21] Appl. No.: 832,549

[22] Filed: Feb. 7, 1992

[51] Int. Cl.$^5$ ............................................. C07D 209/16
[52] U.S. Cl. ..................................... 548/504; 435/121
[58] Field of Search ........................................... 548/504

[56] References Cited

U.S. PATENT DOCUMENTS 4,980,368 12/1990 Thielke et al. .................... 548/504

FOREIGN PATENT DOCUMENTS 0438230 7/1991 European Pat. Off. .

OTHER PUBLICATIONS

Youngdale et al. Chem. Abstracts, vol. 113, No. 23; 211831m (1990).

Primary Examiner—Bernard Dentz
Attorney, Agent, or Firm—Richard C. Billups; Raymond M. Speer

[57] ABSTRACT

An alkyl indole of the formula:

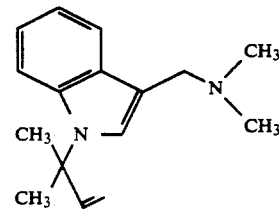

is a useful antimigraine agent.

1 Claim, No Drawings 5,233,050

1

ANTIMIGRAINE ALKYL INDOLE

BACKGROUND OF THE INVENTION

Receptors for 5-hydroxytryptamine (5-HT) are currently classified as $5\text{-}HT_1$-like, $5\text{-}HT_2$ and $5\text{-}HT_3$. The $5\text{-}HT_1$-like class has been further subdivided into $5\text{-}HT_{1A}$, $5\text{-}HT_{1B}$, $5\text{-}HT_{1C}$ and $5\text{-}HT_{1D}$ subtypes. The compound 5-HT has the formula:

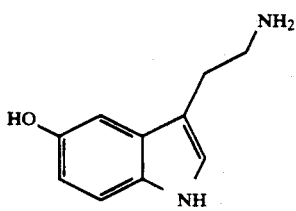

Evaluation of the receptor binding profile of sumatriptan, a potential drug for the acute treatment of migraine, strongly suggests that its stimulation of the $5\text{-}HT_{1D}$ receptor subtype is relevant to the reported antimigraine effects. Sumatriptan is an indole of the formula:

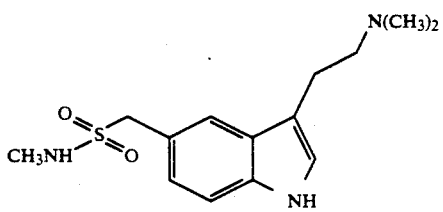

Further compounds to bind the $5\text{-}HT_{1D}$ receptor as well as other 5-HT receptors are of interest to improve migraine treatment.

SUMMARY OF INVENTION

The present invention provides an alkyl indole of the formula:

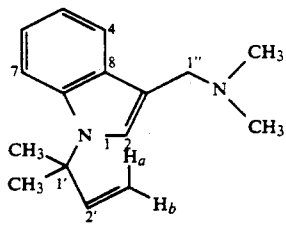

as antimigraine agents as well as a process for making the same.

DETAILED DESCRIPTION OF THE INVENTION

The alkyl indole of formula I is produced by fermentation of *Penicillium daleae*. The particular strain of *Penicillium daleae* employed is deposited as ATCC 74115 and was obtained from Dr. Charles Thom in 1942 (strain no. 260-5034.116, Peoria 920), U.S. Dept. of Agriculture, Peoria, Ill. This strain is maintained at the Merck culture collection in lyophilized form (MF 1134). K. B. Raper and C. Thom, A Manual of the Penicillia, pp 296-299, Williams and Wilkins Co., 1949, state that their original culture of *Penicillium daleae* was lost between 1935 and 1940, but that a new culture was obtained from the Centraalbureau, Baarn, Netherlands, and maintained as NRRL 2025 (ATCC 10435, CBS 211.28). Thus, *Penicillium daleae* is well known and widely available.

Colonies of ATCC 74115 on Czapek's Yeast Autolysate Agar (CYA) were grown to a diameter of 34-36 mm in 7 days at 25° C., radially sulcate, velutinous, mycelium white, conidiophore production moderate to heavy, Russian Green, Sage Green, reverse pale cream (capitalized color names are from Ridgeway, R., 1912, Color Standards and Nomenclature, Washington, D.C.). On CYA at 5° C., microcolonies were formed measuring 3 mm diameter but this strain does not grow an CYA at 37° C. Colonies on 25% Glycerol Nitrate Agar (G25N) grew to 15-17 mm diameter in 7 days, sulcate, velutinous. Colonies on Blakeslee's Malt Extract Agar (MEA) grew to 29-30 mm diameter in 7 days, plane, velutinous, conidiophore production heavy, Dark Glaucous-Gray, Bluish Gray-Green, Light Porcelain Green, reverse pale to yellow-brown. Conidiophores were borne from surface or aerial hyphae, stipes 60-100×2.5 μm, rough, bearing terminal and subterminal metulae, monoverticillate conidiophores also observed. Metulae in groups of 4-6, 7-11×3 μm, conidiogenous cells enteroblastic, phialidic ampulliform in groups of 1-4, 7.6-9.5×3 μm, conidia subspherical, toughened 2.6-3.5 μm.

K. B. Raper and C. Thom described the cultural characteristics of NRRL 2025 as follows: Colonies on Czapek's solution agar attaining a diameter of 4.0 to 4.5 cm. in 12 days to 2 weeks at room temperature (24° C.), producing a rather delicate basal felt with surface growth somewhat floccose and with marked development of funicles often apparent at the colony margin, radially furrowed, almost azonate, white with submarginal zone becoming slightly gray with the very sparse development of conidia, no exudate produced; odor almost lacking, slightly sourish; reverse uncolored to cream; conidia generally borne upon single sterigmata or upon very small clusters of sterigmatic cells, 8 to 12 μ by 2.0 to 2.5 μ with abruptly narrowed apices, arising from aerial hyphae, rarely from structures suggesting true penicilli, elliptical to subglobose, 3.0 to 3.5 μ by 2.5 to 3.0 μ, with coarse roughenings in spirally-arranged bands or bars.

Colonies on steep agar spreading more rapidly, attaining a diameter of 6.0 to 6.5 cm in 12 days, closer textured and more conspicuously furrowed than on Czapek but otherwise duplicating the preceeding.

Colonies on malt agar spreading broadly, up to 8.0 cm in 12 days, loose-textured, but floccose, with surface growth showing a network of aerial hyphae or thin ropes of hyphae, lightly sporulating with penicilli limited in number and almost invariably monoverticillate.

Other apparent subspecies of *Penicillium daleae* are known and readily available. Among these are ATCC 44323, ATCC 44324, ATCC 48647 and ATCC 48648.

In general, the compound of Formula I may be produced by culturing (fermentation) the *Penicillium daleae* in an aqueous nutrient medium containing sources of assimilable carbon and nitrogen, preferably under submerged aerobic conditions (e.g. shaking culture, submerged culture, etc.). The aqueous medium is preferably maintained at a pH of about 7 at the initiation and termination (harvest) of the fermentation process. A higher pH leads to substantial and/or total loss of product. The desired pH may be maintained by the use of a buffer such as morpholinoethanesulfonic acid (MES), morpholinopropanesulfonic acid (MOPS), and the like, or by choice of nutrient materials which inherently possess buffering properties, such as production media described hereinbelow.

The preferred sources of carbon in the nutrient medium are carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium slats (e.g. ammonium nitrate, ammonium sulfate, ammonium phosphate, etc.), urea, amino acids and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts and the like. If necessary, especially when the culture medium foams seriously, a defoaming agent, such as liquid parafffin, fatty oil, plant oil, mineral oil or silicone may be added.

As to the conditions for the production of the compound of Formula I in massive amounts, submerged aerobic cultural conditions are preferred. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tank. The fermentation medium in which the inoculum is produced, is substantially the same as or different from the medium utilized for production and is generally autoclaved to sterilize the medium prior to inoculation. The pH of the medium is generally adjusted to about 7.0 prior to the autoclaving step by suitable addition of an acid or base, preferably in the form of a buffering solution.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°-35° C., for a period of about 10 hours to 40 hours, which may be varied according to fermentation conditions and scales.

The produced compound can be recovered from the culture medium by conventional means which are commonly used for the recovery of other known biologically active substances. The compound substance produced is found in the cultured mycelium and filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methanol and the like, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like. A preferred method is solvent extraction, particularly using methanol.

Suitable salts of the material may include pharmaceutically acceptable salts such as acidic salts, for example, chlorides, acetates etc.

The pharmaceutical composition of this invention can be used in the form of a pharmaceutical preparation, for example, in solid, semisolid or liquid form, which contains the compound of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch urea and other carriers suitable for use in manufacturing preparations, in solid, semisolid, or liquid form and in addition auxiliary, stabilizing, thickening and coloring agents and perfumes may be used. The active object compound is included in the pharmaceutical composition in an amount sufficient to produce the desired effect upon the process or condition of diseases.

For applying this composition to a human, it is preferable to apply if by parenteral or enteral administration. While the dosage of therapeutically effective amount of the compound, varies from and also depends upon the age and condition of each individual patient to be treated, a daily dose (calculated on the basis of a 70 kg man) of about 0.01–1000 mg. preferably 0.1–500 mg and more preferably 0.5–100 mg. of the active ingredient is generally given for treating diseases, and an average single dose of about 0.5 mg, mg. 5 mg, 10 mg, 50 mg, 100 mg, 250 mg and 500 mg is generally administered.

EXAMPLES

*Penicillium daleae*, as described, was added under aseptic conditions to 54 ml of a seed medium in a 250-ml plain Erlenmeyer flask. The seed medium consisted of yeast extract (Difco) 0.4%, malt extract (Difco) 1% and glucose 0.4%, pH 7.0. The flask was maintained at 22° C. on a rotary shaker for 3 days. A second stage seed culture was obtained by repeating the above procedure using 1 ml of the first seed culture as inoculum per flask and incubated for 2 day. A 24 ml inocolum from the second seed culture was added to 425 ml of the liquid phase of production medium in a 1-liter Erlenmeyer flask. The liquid phase of the production medium consisted of glucose 1%, fructose 1.5%, sucrose 4%, NZ amine type E (Sheffield Products) 0.4%, urea 0.4%, $K_2HPO_4$ 0.05%, KCl 0.025% m $MgSO_4 \cdot 7H_2O$ 0.025%, $ZnSO_4 \cdot 7H_2O$ 0.09% and $CaCO_3$ 0.8%. This liquid phase and seed mixture was mixed vigorously with 1250 ml of vermiculite, as the solid phase, in a 4-liter roller jar. Incubation was then performed at 22° C. on a roller machine for 19 days.

Fermentation in eight roller jars was extracted with methyl ethyl ketone (5600 ml) for three hours at room temperature. Filtration over Whatman number 3 filter paper and flash evaporation afforded 6 g dry weight. Partition between water (20 ml) and methyl ethyl ketone (4×30 ml) yielded 2 g dry weight from the organic layers. Preparative chromatographic purification included three columns: a) Whatman partisil 10 ODS-3 (2.3×50 cm) using 20-25% acetonitrile in 0.1% TFA (aq) as mobile phase; b) E. Merck silica gel 60 (20 g, 40-63 μm, 2.5×10 cm) using 0.5% triethylamine in Me2CO/hexane mixtures as mobile phase; and c) Whatman partisil 10 ODS-3 (0.94×50 cm) using 20-25% acetonitrile/0.1% TFA (aq) as mobile phase. The actual sequence consisted of two rounds on a), once on b), once on a) again, and then once on c). 35 mg of homogeneous I was obtained in this fashion with a $R_f$ of 0.17 [E. Merck silica gel 60F, 0.2 mm thickness, hexane-acetone-triethylamine, 50:50:0.5] and a k' of 4.72 [Whatmann partisil 5 ODS-3, acetonitrile-0.1% TFA (aq), 3:7].

The physico-chemical properties of I are as follows: $UV\lambda_{max}MeOH_{nm}(E^{1\%}_{1\ cm})$ 219 (484), 267 (118), 279 (114), 290 (93); FT-IR $\nu_{max}$(ZnSe) cm$^{-1}$ 2984, 1679, 1550, 1458, 1202, 1138; HREI-MS m/z 242.1766 (M, Calcd for $C_{16}H_{22}N_2$: 242.1783), 198 [M—N(CH$_3$)$_2$], 173 [M—C(CH$_3$)$_2$(CH=CH$_2$)], 130.0636 (base peak, for $C_9H_8N$: 130.0657).

The physico-chemical properties agree with the assignment of structure I or 1-(1,1-dimethylallyl)-3-dimethylaminomethylindole.

5-HT$_{1D}$ radioligand binding assay was carried out according to Heuring and Peroutka (Heuring, R. E., and Peroutka, S. J., J. Neurosci., 7:894-903, 1987) with slight modifications as follows. Polypropylene tubes containing $^3$H-5HT (2 nM), cyanopindolol (100 nM), mesulergine (100 nM) and crude pig striatal membranes (10 mg wet weight per tube) in a final assay volume of 1 ml were used. All reagents and tissues were made up in 50 nM Tris. HCl containing 0.1% ascorbate, 10 μM pargyline and 4 mM CaCl$_2$ (pH 7.7 at room temperature). 5-HT (10 μM) was used to define non-specific binding. The incubation was initiated by the addition of membranes and carried out for 30 minutes at 37° C. Following incubation, membranes were rapidly filtered under vacuum through Whatmann GF/B filters using a Brandel Cell Harvester, followed by 2×3 ml washes with 50 mM Tris. HCl (pH 7.7 at room temperature). Bound radioactivity was determined by liquid scintillation spectrometry. 5-HT$_{1A}$ and 5-HT$_2$ radioligand binding assays were performed according to Hall, et al., J. Neurochem., 44, 1685-1696, 1985 and Titeler, et al., Eur. J. Pharmacol., 117, 145-146, 1987, respectively. Results of these binding assays are presented as the mean of triplicates in table I. Compound I has less affinity for 5-HT$_{1A}$ than for 5-HT$_{1D}$ and 5-HT$_2$ receptor subtypes, for which it has similar affinity and thus is not selective between the latter two. For comparison, sumatriptan shows a rank order of affinity for these subtypes: 5-HT$_{1D}$>5-HT$_{1A}$>5-HT$_2$ with pIC$_{50}$'s of 7.7, 6.3 and <5.0 respectively.

TABLE I

| | Binding of Compound I to 5-HT receptor subtypes, % inhibition | |
|---|---|---|
| Assay | 4.1 μM | 41 μM |
| 5-HT$_{1D}$ | 44 | 81 |
| 5-HT$_{1A}$ | 20 | 62 |
| 5-HT$_2$ | 42 | 86 |

What is claimed is:
1. A compound of the structure:

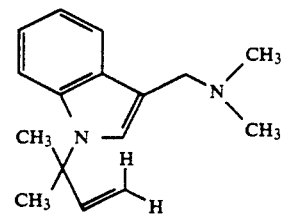

* * * * *